US012180306B2

(12) United States Patent
Hsu et al.

(10) Patent No.: US 12,180,306 B2
(45) Date of Patent: Dec. 31, 2024

(54) ANTI-ALLERGIC PEPTIDE AND USE THEREOF FOR IMMUNE REGULATION AND ANTI-ALLERGY

(71) Applicant: Greenyn Biotechnology Co., Ltd, Taichung (TW)

(72) Inventors: Pang Kuei Hsu, Taichung (TW); Yu Cheng Lin, Taichung (TW); Chih Kuo Kao, Taichung (TW); Chia Feng Wu, Taichung (TW)

(73) Assignee: GREENYN BIOTECHNOLOGY CO., LTD, Taichung (TW)

( * ) Notice: Subject to any disclaimer, the term of this patent is extended or adjusted under 35 U.S.C. 154(b) by 0 days.

(21) Appl. No.: 18/061,238

(22) Filed: Dec. 2, 2022

(65) Prior Publication Data
US 2023/0322855 A1    Oct. 12, 2023

(30) Foreign Application Priority Data
Apr. 11, 2022  (TW) .................................. 111113738

(51) Int. Cl.
C07K 7/00    (2006.01)
A61P 37/08   (2006.01)
C07K 7/06    (2006.01)

(52) U.S. Cl.
CPC ............... C07K 7/06 (2013.01); A61P 37/08 (2018.01)

(58) Field of Classification Search
CPC .................................. C07K 7/06; A61P 37/08
See application file for complete search history.

(56) References Cited

U.S. PATENT DOCUMENTS

2009/0257993 A1* 10/2009 M'Rabet ................. A61P 29/00
                                                     435/252.9

OTHER PUBLICATIONS

Villena et al. Draft genome sequence of Lactobacillus plantarum MPL16, an immunobiotic strain isolated from pig intestine, Genome Announcements, vol. 5, No. 10, Mar. 2016.*

Pearson, William. An Introduction to Sequence Similarity ("Homology") Searching. Curr. Protoc. Bioinformatics, 2013.*
Sun et al. (2015) Nature Communications, 6:8322, DOI: 10.1038/ncomms9322. www.nature.com/naturecommunications.*
Gong et al. Frontiers in Immunology, vol. 11, 2011.*
Markova et al. PNAS. Oct. 17, 2006 . vol. 103 No. 42. p. 15611-15616.*
Database UniProt (on line), Feb. 28, 2018 (Feb. 28, 2018), "SubName: Full=calcium-transporting ATPase 1 {ECO:0000313 EMBL:QHM37110.1}", XP002809866, retrieved from EBI accession No. UNIPROT: A0A210YZE6 Database accession No. A0A210YZE6.
Database UniProt (on line), May 23, 2018 (May 23, 2018), "SubName: Full=Major tail protein {ECO:0000313 EMBL: AVH85803.1}", XP002809869, retrieved from EBI accession No. UNIPROT: A0A2POZLF5 Database accession No. A0A2POZLF5.
Database UniProt (on line), Oct. 7, 2020 (Oct. 7, 2020), "RecName: Full=Permease {ECO:0000256 Google: ProtNLM}", XP002809870, retrieved from EBI accession No. UNIPROT: A0A6N4RKU8 Database accession No. A0A6N4RKU8.
Database UniProt (on line), Apr. 22, 2020 (Apr. 22, 2020), "RecName: Full=Histudine protein kinase sensor protein [Lactobacillus plantarum JDM1] {ECO:0000313 VDG30266.1}", XP002809871, retrieved from EBI accession No. UNIPROT: A0A660E2B6 Database accession No. A0A660E2B6.
K. E. Fujimura et al., "House dust exposure mediates gut microbiome Lactobacillus enrichment and airway immune defense against allergens and virus infection", Proceedings of the National Academy of Sciences, vol. 111, Issue 2, 2014, pp. 805-810.
CAD65500, cation transporting P-type ATPase , GenPept[online] , Feb. 4, 2011 , https://www.ncbi.nlm.nih.gov/protein/28272574?sat=2&satkey=29821826.
CAD65138, 3-octaprenyl-4-hydroxybenzoatecarboxy-lyase , GenPept[onlin e] , Feb. 4, 2011 , https://www.ncbi.nlm.nih.gov/protein/28272230?sat=2&satkey=29821824.

* cited by examiner

Primary Examiner — Jeanette M Lieb
(74) Attorney, Agent, or Firm — Muncy, Geissler, Olds & Lowe, P.C.

(57) ABSTRACT

The invention provides an anti-allergic peptide and a use thereof for immune regulation and anti-allergy, the anti-allergic peptide is capable of inhibiting secretion of cytokines related to allergic reactions and regulating allergic reactions, and the anti-allergic peptide comprises an amino acid sequence shown in SEQ ID No: 1, SEQ ID No: 2, SEQ ID No: 3, SEQ ID No: 4 or SEQ ID No: 5, or a homologous amino acid sequence derived from substitution, deletion, and addition of one amino acid or more than one amino acid of any of the above sequences.

2 Claims, 13 Drawing Sheets

Specification includes a Sequence Listing.

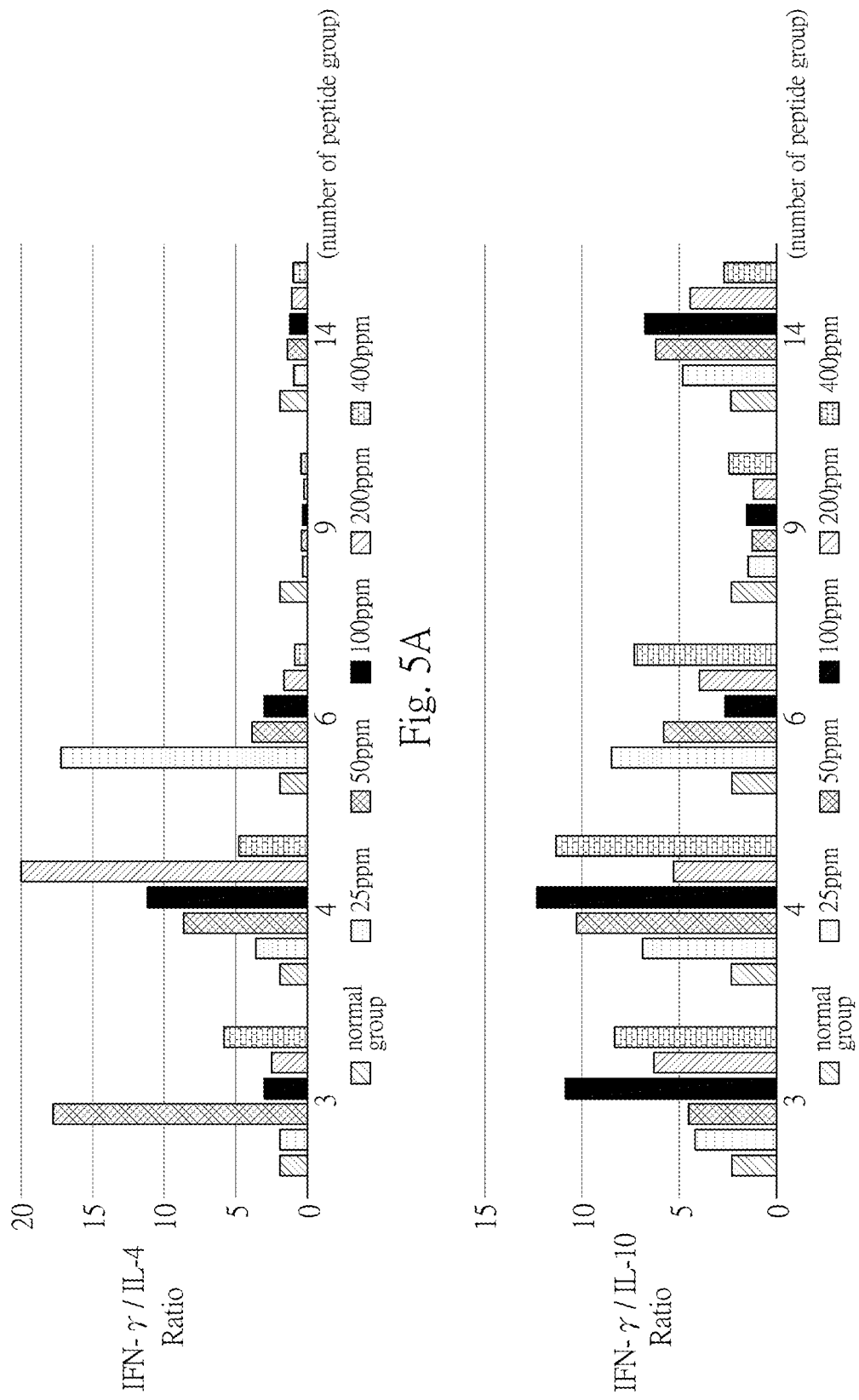

ANTI-ALLERGIC PEPTIDE AND USE THEREOF FOR IMMUNE REGULATION AND ANTI-ALLERGY

REFERENCE TO AN ELECTRONIC SEQUENCE LISTING

The content of the electronic sequence listing (sequence_listing.xml; Size: 14,775 bytes; and Date of Creation, Dec. 1, 2022) is herein incorporated by reference in its entirety.

FIELD OF THE INVENTION

The invention relates to a peptide and a use thereof, more particularly to an anti-allergic peptide and a use thereof for immune regulation and anti-allergy.

DESCRIPTION OF THE RELATED ART

The immune system is the body's defense system against foreign pathogens. When the immune system is normal, it can distinguish between pathogens and foreign harmful substances, and activate the defense mechanism; when parts of the immune system are inactivated, it can cause a decrease in immunity or a deficiency of immune function, which not only cannot block all pathogens, leading to an increased risk of illness, but also an increased risk of cancer; and when the immune system is overactive, it can lead to diseases related to immune system disorders, which means that the immune system cannot distinguish between autoantigens and alloantigens and attacks its own cells. In other words, an immunoreaction that is too low or too high has an adverse effect on human health. Therefore, how to regulate the immune system and maintain it in a balanced state is an important health issue for modern people.

There are many reasons for immune imbalance, including too little sleep, too much stress, excessive fatigue, insufficient exercise, and unbalanced nutrition. Therefore, the current clinical recommendations for immune regulation include regular work and rest, moderate exercise and nutritional balance. In fact, it is difficult for the vast majority of modern people to change their living and eating habits. Therefore, they often improve their internal environment by supplementing supplements such as probiotics, vitamin C, and vitamin D to regulate the immune system. However, there are many products on the market that claim to be able to regulate immunity, which is not only difficult to choose, but also can cause a burden on the body due to excessive use.

SUMMARY OF THE INVENTION

A main object of the invention is to provide an anti-allergic peptide and a use thereof for immune regulation and anti-allergy. Specifically, the anti-allergic peptide is capable of inhibiting cells from secreting cytokines and maintaining balance of Th1/Th2 ratio after immunostimulation. Therefore, the anti-allergic peptide disclosed in the invention is capable of being used in improving an individual's anti-allergic reactions and capable of regulating the individual's immunity in order to effectively achieve efficacies of preventing the individual from being invaded by foreign substances or pathogenic bacteria and also preventing the individual's immunoreaction from being too strong.

In order to achieve the above object, the invention provides an anti-allergic peptide capable of being prepared by artificial synthesis or biosynthesis, and capable of resisting allergy and regulating immunity; that is, by administering an effective amount of the anti-allergic peptide or its metabolites disclosed in the invention to an individual is capable of improving the individual's allergic reactions and symptoms and achieving an efficacy of regulating respiratory allergy and immunity.

In one embodiment of the invention, an amino acid sequence coding of the anti-allergic peptide comprises the sequence shown in SEQ ID No: 1, SEQ ID No: 2, SEQ ID No: 3, SEQ ID No: 4 or SEQ ID No: 5, or a homologous amino acid sequence derived from substitution, deletion, and addition of one amino acid or more than one amino acid of any of the above sequences.

In one embodiment of the invention, an amino acid sequence of the anti-allergic peptide is encoded as SEQ ID No: 1, SEQ ID No: 2, SEQ ID No: 3, SEQ ID No: 4 or SEQ ID No: 5.

Wherein the anti-allergic peptide disclosed in the invention is isolated from a fermentation product of lactic acid bacteria, and particularly refers to a fermentation product of *Lactobacillus plantarum*.

Wherein the anti-allergic peptide disclosed in the invention is synthesized artificially.

Since the anti-allergic peptide disclosed in the invention is capable of inhibiting secretion of cytokines such as IL-4 and IL13 by cells, and capable of regulating indicators related to Th1 or Th2 immune pathway in serum, such as IgE and IgG, the anti-allergic peptide disclosed in the invention is capable of being used in preparing a composition for improving allergy and/or regulating immunity.

In another embodiment of the invention, a method for immune regulation or anti-allergy is disclosed. The method for immune regulation or anti-allergy comprises administration a composition including an effective amount of the anti-allergic peptide disclosed in the invention to an individual with allergic disease to achieving an efficacy of effectively improving the individual's anti-allergic ability, alleviating the individual's allergic symptoms or maintaining the individual's immunity.

Wherein, the composition contains an effective amount of the anti-allergic peptide disclosed in the invention, such as the anti-allergic peptide with an amino acid sequence encoded as any one of SEQ ID No: 1 to SEQ ID No: 5.

Wherein, the allergic disease is allergy or asthma.

In another embodiment of the invention, the composition five peptides with the amino acid sequences encoded as SEQ ID No: 1 to SEQ ID No: 5.

Wherein the composition is a fermentation product of lactic acid bacteria.

BRIEF DESCRIPTION OF DRAWINGS

FIG. 5A is the analyzed result of a concentration ratio of IFN-γ/IL-4 secreted by spleen cells of mice in an OVA-induced group after the spleen cells of the mice in the OVA-induced group are respectively cultured in a medium supplemented with different concentrations of each of the peptide groups.

FIG. 5B is the analyzed result of a concentration ratio of IFN-γ/IL-10 secreted by the spleen cells of the mice in the OVA-induced group after the spleen cells of the mice in the OVA-induced group are respectively cultured in a medium supplemented with different concentrations of each of the peptide groups.

DETAILED DESCRIPTION OF THE INVENTION

Figure 1A:
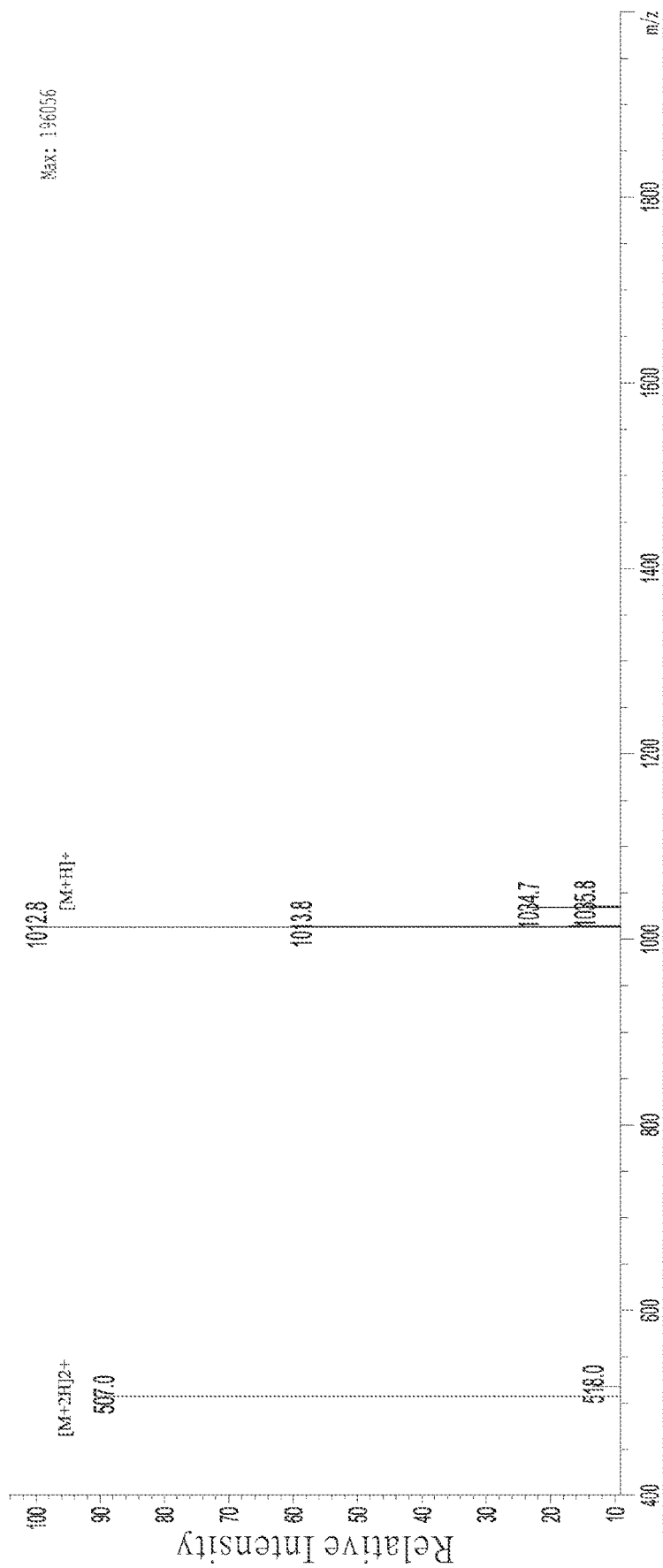
FIG. 1A is a mass spectrogram analysis of a peptide sequence encoded as SEQ ID No: 1.
Figure 1B:
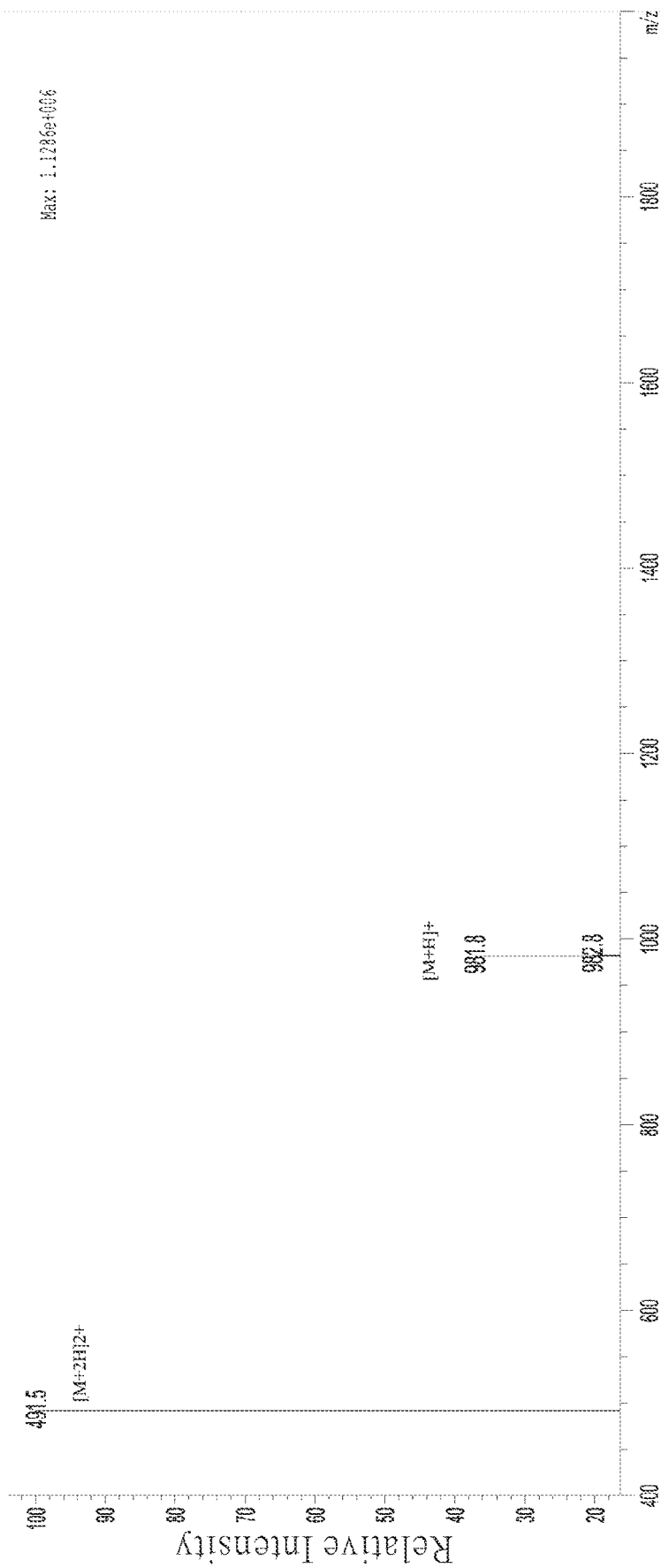
FIG. 1B is a mass spectrogram analysis of the peptide sequence encoded as SEQ ID No: 2.
Figure 1C:
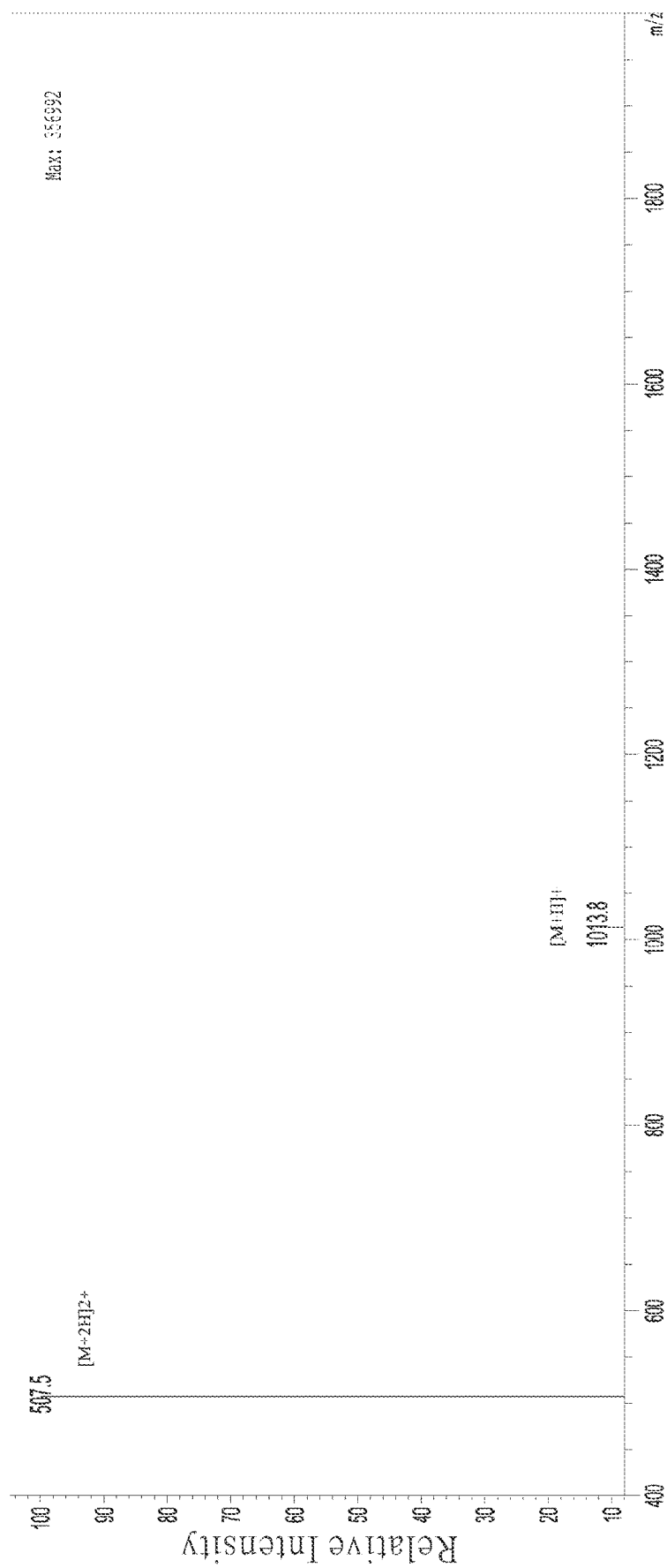
FIG. 1C is a mass spectrogram analysis of the peptide sequence encoded as SEQ ID No: 3.
Figure 1D:
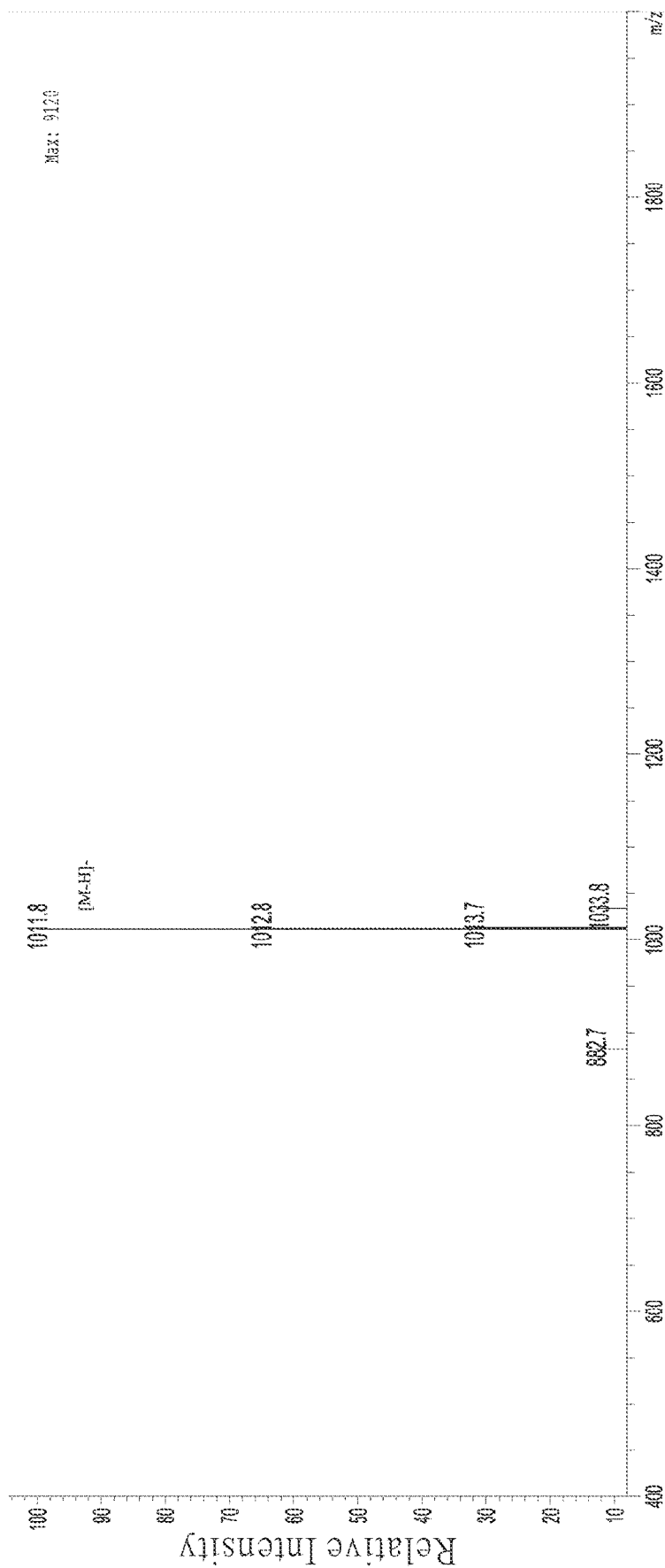
FIG. 1D is a mass spectrogram analysis of the peptide sequence encoded as SEQ ID No: 4.
Figure 1E:
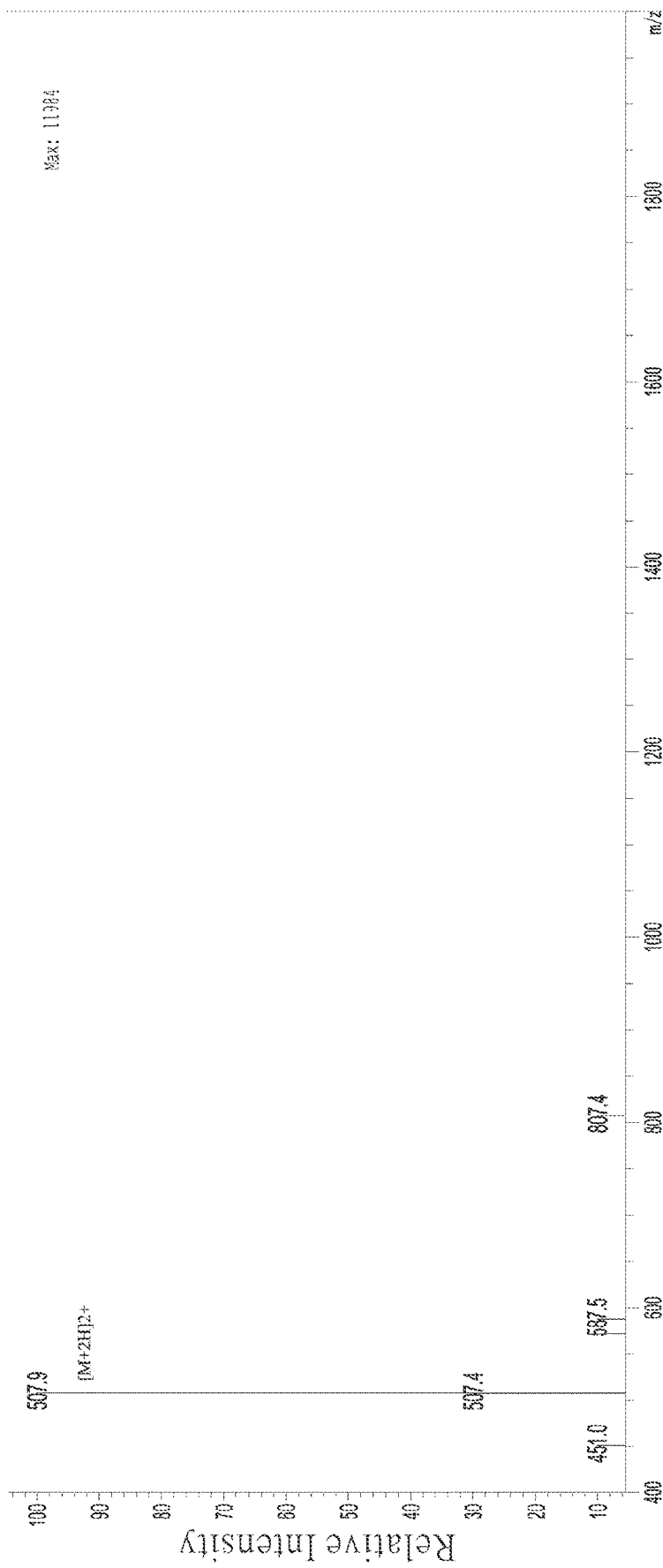
FIG. 1E is a mass spectrogram analysis of the peptide sequence encoded as SEQ ID No: 5.
Figure 2A:
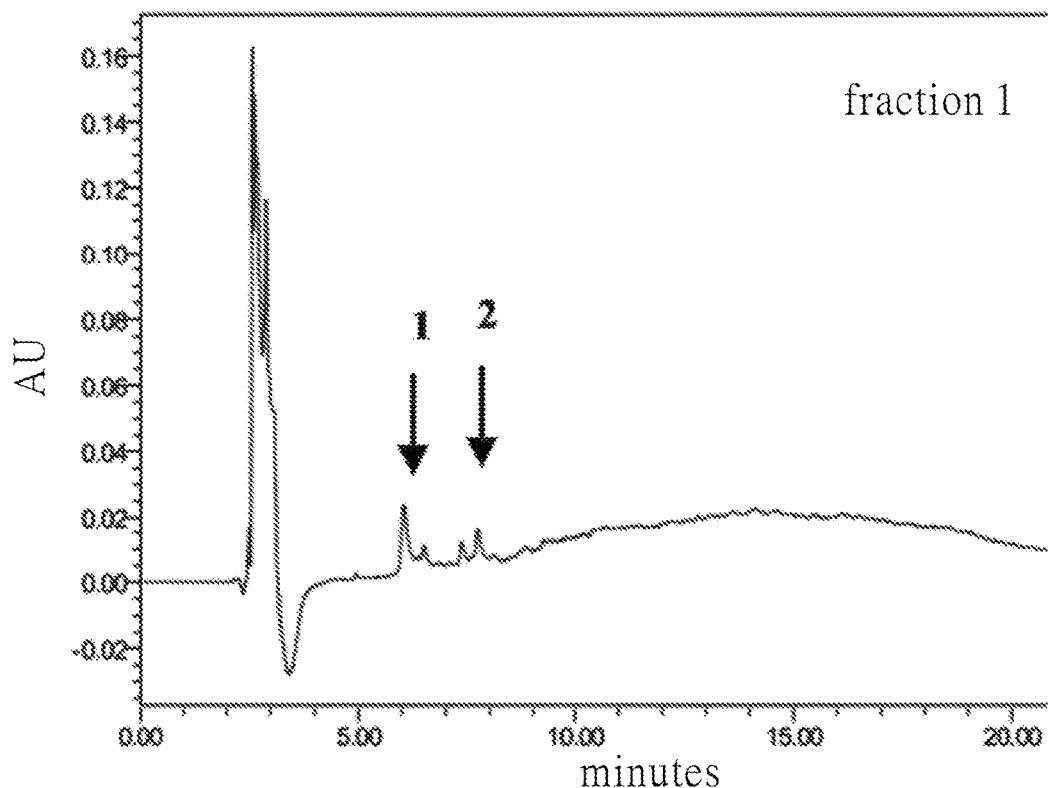
FIG. 2A is the result of C18 chromatographic separation of distinct fragment 1 in an extracellular fermentation broth of lactic acid bacteria, wherein arrow 1 is a first peptide group, and arrow 2 is a second peptide group.
Figure 2B:
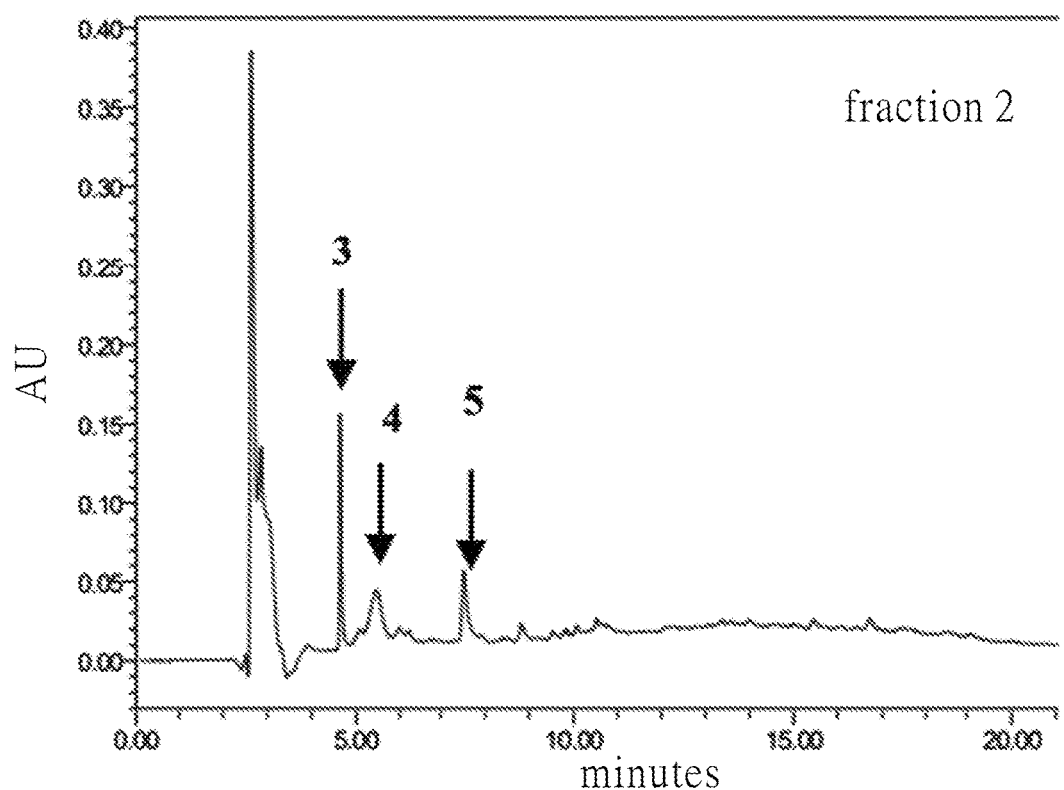
FIG. 2B is the result of C18 chromatographic separation of distinct fragment 2 in the extracellular fermentation broth of lactic acid bacteria, wherein arrows 3 to 5 represent a third peptide group to a fifth peptide group in sequence.
Figure 2C:
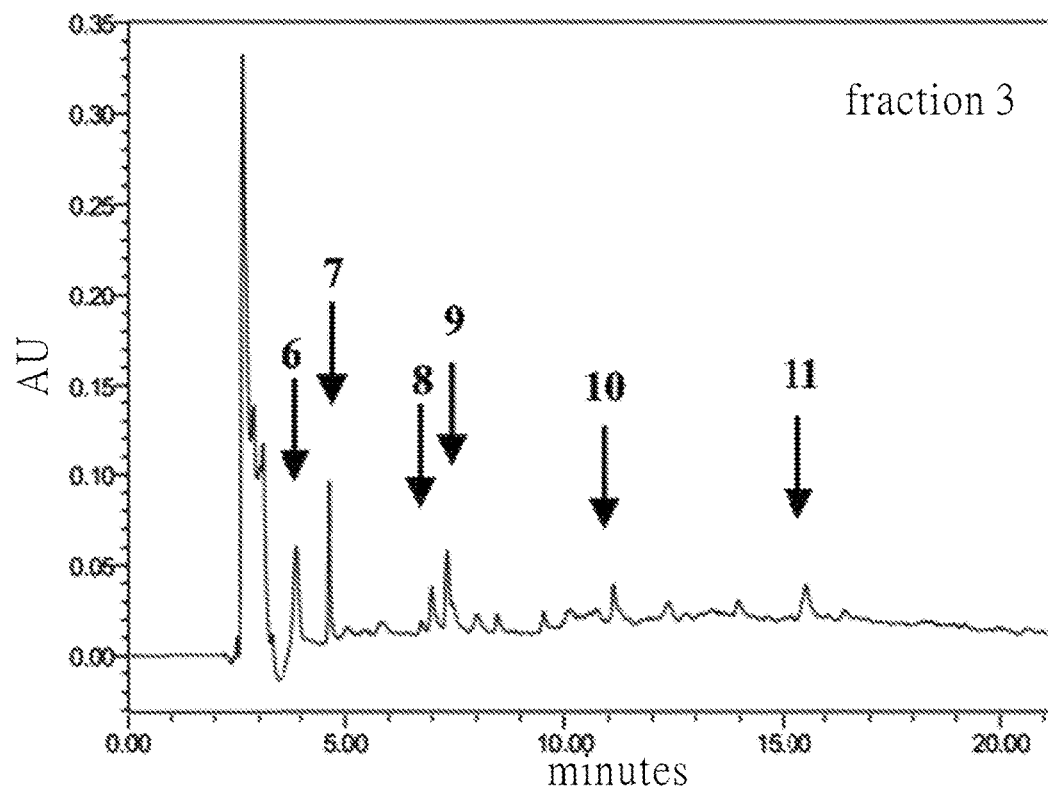
FIG. 2C is the result of C18 chromatographic separation of distinct fragment 3 in the extracellular fermentation broth of lactic acid bacteria, wherein arrows 6 to 11 represent a sixth peptide group to an eleventh peptide group in sequence.
Figure 2D:
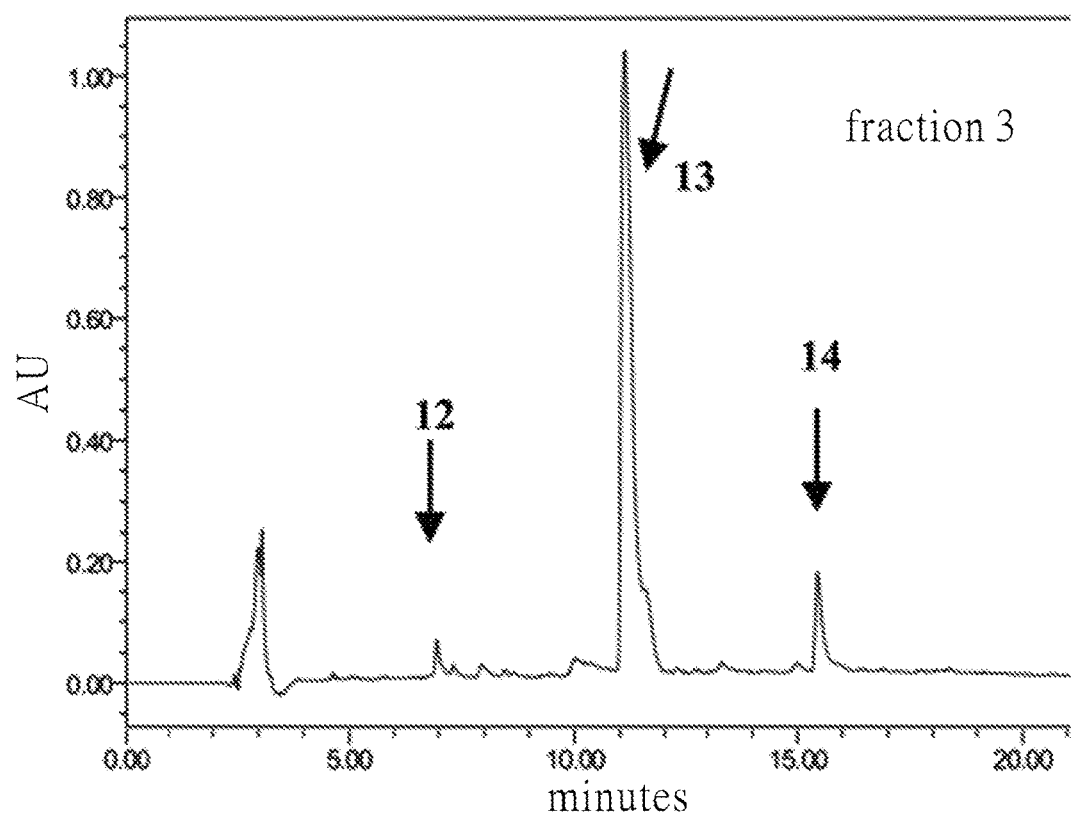
FIG. 2D is the result of C18 chromatographic separation of distinct fragment 4 in the extracellular fermentation broth of lactic acid bacteria, wherein arrows 12 to 14 represent a twelfth peptide group to a fourteenth peptide group in sequence.

The invention discloses an anti-allergic peptide or its metabolites capable of regulating immunity and resisting allergy, and capable of being used as a main component in a composition for improving allergic symptoms or/and regulating immunity. Specifically, an amino acid sequence of the anti-allergic peptide comprises the sequence encoded as SEQ ID No: 1, the sequence encoded as SEQ ID No: 2, the sequence encoded as SEQ ID No: 3, the sequence encoded as SEQ ID No: 4, the sequence encoded as SEQ ID No: 5, or a homologous amino acid sequence derived from substitution, deletion, and addition of one amino acid or more than one amino acid of any of the above sequences.

In one embodiment of the invention, an amino acid sequence of the peptide is encoded as SEQ ID No: 1, SEQ ID No: 2, SEQ ID No: 3, SEQ ID No: 4 or SEQ ID No: 5, and a molecular weight of each of the peptides is shown in Table 1 below, and the mass spectrogram analysis of each of the peptides is shown in FIG. 1A to FIG. 1E.

TABLE 1

Molecular weight of the peptide disclosed in the invention

| Peptide sequence code | Amino acid sequence | Molecular weight (Da) |
|---|---|---|
| SEQ ID No: 1 | DLQLAGLIGL | 1012.2006 |
| SEQ ID No: 2 | NPALQVIKV | 981.1899 |
| SEQ ID No: 3 | GLGDAKVALGI | 1013.1887 |
| SEQ ID No: 4 | EWLLGLLGI | 1013.2341 |
| SEQ ID No: 5 | DLDVVVALGI | 1013.1854 |

The so-called "homologous amino acid sequence" in the invention means that the protein expressed by it has structural and functional similarity with the peptide disclosed in the invention, which means that the homologous amino acid sequence is highly similar to the amino acid sequence of the peptide disclosed in the invention, and immune regulation and anti-allergic functions are not affected.

The anti-allergic peptide disclosed in the invention is capable of being prepared by techniques well known to a person having ordinary skill in the art to which the invention pertains, such as artificial synthesis methods, biosynthesis methods. Specifically, artificial synthesis methods include chemical synthesis, liquid-phase peptide synthesis, solid-phase peptide synthesis or peptide synthesizers; biosynthesis methods include transferring nucleic acid molecules of target peptides into a microorganism through genetic recombination, the recombinant microorganism is then fermented and cultured to express a large amount of target peptides, and then a large amount of target peptides can be obtained through steps such as separation and purification, wherein, currently, in order to comply with relevant food safety regulations, the microorganism used is mainly strains or bacterial species that are harmless to the human body, such as yeast, lactic acid bacteria, etc.

For example, the anti-allergic peptide disclosed in the invention is capable of being produced by fermenting lactic acid bacteria, such as *Lactobacillus plantarum, Lactobacillus reuteri, Lactobacillus brevis*, or bacterial species highly homologous with any of the above-mentioned lactic acid bacteria that served as a mother starter in a microbial production platform, which means that the lactic acid bacteria for expressing the peptide disclosed in the invention are subjected to liquid fermentation culture, culture medium is modified MRS, cultured temperature is 30-45° C., a supernatant liquid is obtained after fermentation and culture, and the supernatant liquid contains the peptide disclosed in the invention, which can be separated and purified by gel permeation chromatography separation, column chromatography analysis, reversed-phase chromatography, HPLC (high performance liquid chromatography); wherein in order to increase production efficiency, the fermentation conditions used are adjusted according to ordinary skill in the art to which the invention pertains, such as adjusting a pH value of the medium through sodium hydroxide.

Wherein the modified MRS medium disclosed in the invention refers to the MRS medium used as a basis that is well known in the art to which the invention pertains, and carbon source, nitrogen source and other additives in the medium are adjusted, wherein carbon source can be sucrose, lactose, glucose or any other substances used in the art; and nitrogen source can be peptone, beef extract, yeast extract, or a composition of at least any two of the above.

In one embodiment of the invention, in order to obtain the anti-allergic peptide disclosed in the invention by the above-mentioned microorganism production platform, after fermentation of the microorganism is completed, the anti-allergic peptide disclosed in the invention is separated from a fermentation broth. Generally speaking, HPLC is used for separation first. The specific method is to centrifuge the fermentation broth obtained by fermentation and culture. Centrifugation conditions are 6,000 g, 30 minutes, and 4° C. After the supernatant liquid is obtained, it is then respectively filtered with 10 kDa and 3 kDa molecular sieves in sequence to screen out a filtrate containing peptide groups disclosed in the invention, which is pale yellow; then, the peptide groups in the filtrate containing the peptide disclosed in the invention are separated by gel permeation chromatography column analysis with a mobile phase containing salts such as $Na_2HPO_4$, NaCl, $NaH_2PO_4 \cdot 2H_2O$, and positions of standard products, such as Aprotinin 6,500 Da, Vitamin B12 1,350 Da, Cytidine 243 Da are analyzed, after comparing with analysis results of the filtrate, peaking times of four main peptide groups can be distinguished from the gel permeation chromatography column separation map of the filtrate; and then a C-18 column is used to separate the peptide disclosed in the invention from the four peptide groups.

Wherein the lactic acid bacteria used in the invention, such as *Lactobacillus plantarum*, are capable of being used in a fermentation process of a biological production platform after being amplified and cultured through ordinary skill in the art to which the invention pertains.

The "composition" disclosed in the invention refers to at least containing an effective amount of any one of the anti-allergic peptides disclosed in the invention, or its metabolites, or the peptide groups with the anti-allergic peptide disclosed in the invention as a main active ingredient, so that the composition is capable of effectively inhibiting secretion of cytokines such as IL-13, IL-4, IL-10, and effectively reducing allergic phenomenon tending to the imbalance of Th2 ratio; since any of the peptides disclosed in the invention with an amino acid sequence encoded as SEQ ID No: 1 to SEQ ID No: 5 has an efficacy of regulating immunity, when the composition contains more than any two of the peptides disclosed in the invention, a ratio of the peptides can be configured according to ordinary skill in the art to which the invention pertains. For example, all the peptides are proportioned in equal or nearly equal ratios, which does not affect an efficacy that can be achieved in the invention.

The "effective amount" disclosed in the invention means that the peptide disclosed in the invention accounts for 0.01% to 100% of the whole anti-allergic composition or an intake amount is 25 µg or more, when the anti-allergic peptide disclosed in the invention or its metabolites does not/do not constitute the whole of the composition, the composition can contain a food or a pharmaceutically acceptable carrier. Further, the composition can be a medicine, a nutritional supplement, a functional food, a health food or other edible items that contribute to human health.

Hereinafter, in order to illustrate and verify the technical features disclosed in the invention and their efficacies, a number of experimental examples will be provided and described with reference to the accompanying drawings.

The peptides used in the following examples are synthesized by Fmoc method, and correctness and purity of each of the peptides have been verified by methods well known in the art to which the invention pertains, and a purity of each of the peptides is greater than 90%.

Cells used in the following examples can be easily obtained by a person having ordinary skill in the art to which the invention pertains, so they do not need to be deposited. For example, the mouse mast cells P815 are purchased from the Bioresource Collection and Research Center (BCRC for short).

*Lactobacillus plantarum* used in the following examples has a confirmed similarity of 99%-100% after performing PCR with the target genes pgm, ddl, gyrB, purK1, gdh, mutS, tkt as primers, and the results are compared with the biological DNA database sequences of the National Center for Biotechnology Information (NCBI); this bacterial species is a microorganism that can be easily obtained by a person having ordinary skill in the art to which the invention pertains, so it does not need to be deposited, wherein the sequences of the above-mentioned primers are well known in the art to which the invention pertains, so they will not be repeated here.

Compound 48/80 disclosed in the following examples is a polymer produced by the condensation of N-methyl-p-methoxyphenethylamine with formaldehyde, which has efficacies of promoting histamine release, and promoting mast cell degranulation, and is therefore used in the following examples as an allergen that stimulates mast cells to produce allergic reactions.

Mice used in the following examples are 5-week-old female BALB/c strain mice, which are reared in an independent ventilation environment. During the test, they are given general standard feed and sterilized distilled water, temperature is controlled at 23±3° C., relative humidity is 60±10%, with a 12-hour light/dark exchange for illumination time; the following examples are performed starting with mice acclimated to 6 weeks of age.

Example 1: Preparation of Peptide Composition

*Lactobacillus plantarum* is expanded and cultivated in a liquid fermentation tank with the modified MRS medium, and culture temperature is controlled at 35-40° C. After fermentation, a supernatant liquid is obtained by centrifugation and filtration, and an extracellular fermentation broth of lactic acid bacteria is obtained, wherein the centrifugation conditions are 6,000 g, 30 minutes, and 4° C.; and filtration is performed with 10 kDa and 3 kDa molecular sieves.

Wherein the modified MRS medium is based on MRS, added with yeast extract, yeast peptone and soybean peptone as nitrogen sources, and added with 0.1% serine.

Example 2: Separation of Peptide Groups

The extracellular fermentation broth of lactic acid bacteria obtained in Example 1 is separated by a gel permeation chromatography (GPC) column according to a molecular size of the protein, an embankment phase contains mobile phases such as $Na_2HPO_4$, $NaCl$, $NaH_2PO_4 \cdot 2H_2O$, molecular weight is qualitatively determined with standard products Aprotinin (6,500 Da), Vitamin B12 (1,350 Da) and Cytidine (243 Da), the extracellular fermentation broth of lactic acid bacteria is divided into four distinct fragments, and then reversed-phase chromatography supplemented by a non-polar stationary phase column (C18 column) are used according to polarity differences of individual peptides and their affinities for organic solvents to obtain 14 peptide groups, as shown in FIG. 2A to FIG. 2D.

Example 3: Analysis of Ability in Regulating Allergy

Mouse mast cells P815 without adding any peptide are taken, and cultured in an environment of adding 10 μg/mL compound 48/80 for 6 hours, and concentrations of IL-4, IL-13 of the cells are tested at 0, 0.5, 2, 4, and 56 hours of the experiment, it is found that the concentration of IL-13 increases during the period of 4-6 hours, and the concentration of IL-13 increases by 74.1% from 0.5 hours to 6 hours. The results show that adding the compound 48/80 is capable of reliably constructing an allergic cell model, and therefore, the 14 peptide groups are tested for a potential of inhibiting allergic reactions and regulating immunity through the model induced by the compound 48/80 in the mouse mast cells P815, which means that after the 14 peptide groups are respectively placed in a culture environment with the mouse mast cells P815, and the compound 48/80 (10 μg/mL) is added to the culture environment of each of the groups of the cells to detect and analyze an ability of each of the peptide groups in inhibiting secretion of IL-4 and IL-13 by the mouse mast cells P815, the results are shown in FIG. 3.

Figure 3:
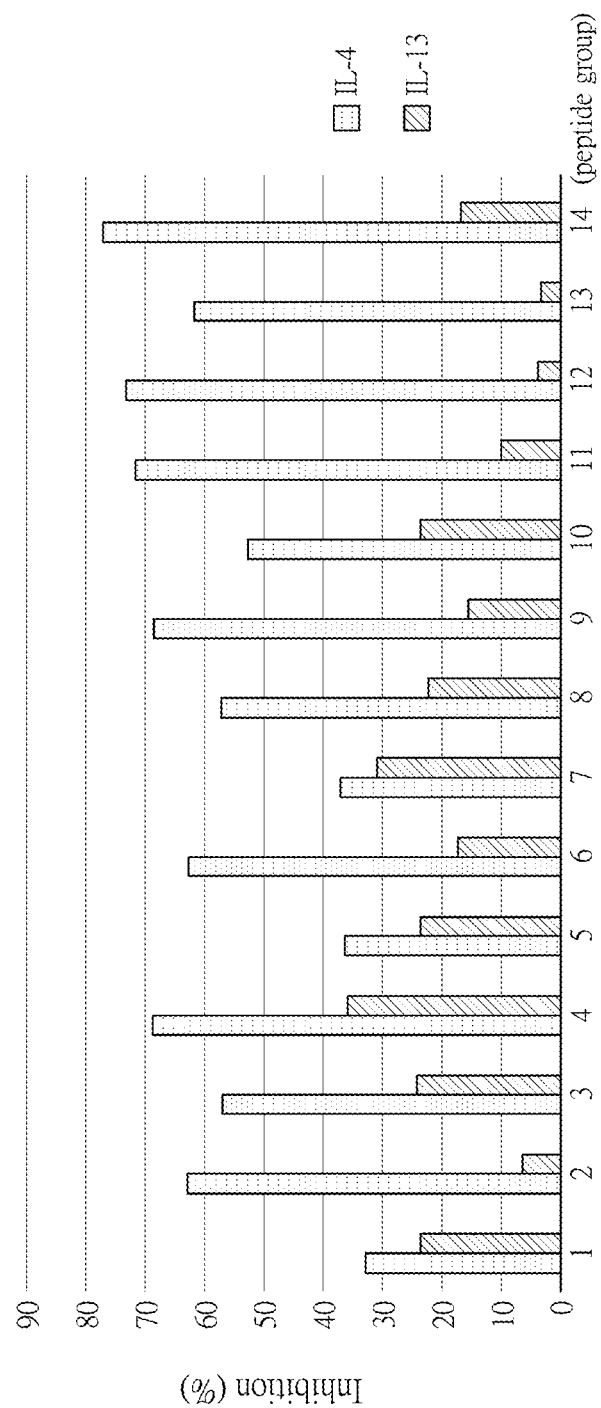
FIG. 3 is the result of detecting and analyzing a percentage of each of the peptide groups in inhibiting secretion of IL-4 and IL-13.
Figure 4A:
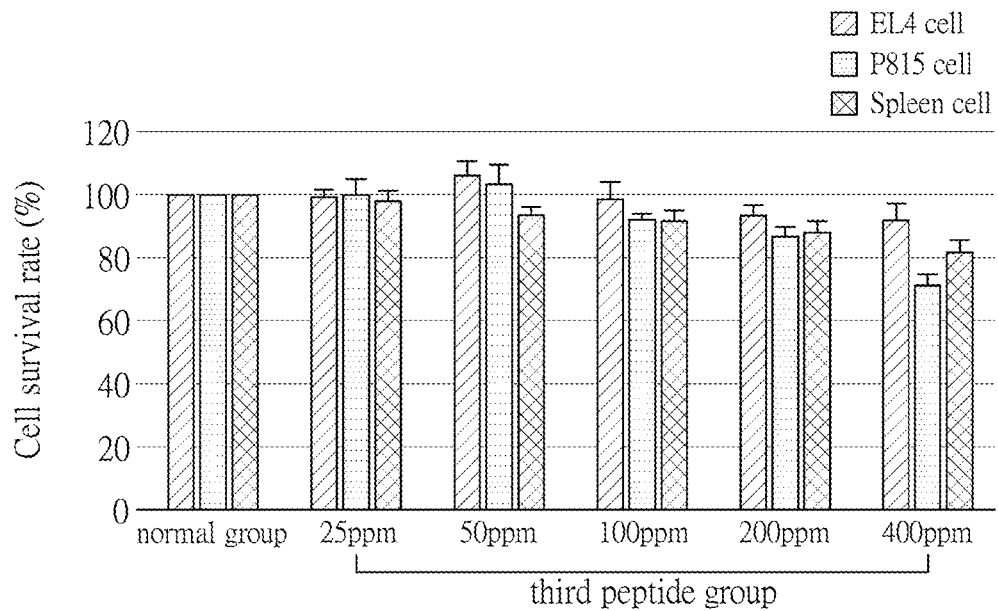
FIG. 4A is the result of detecting survival rates of mouse EL4 lymphoma cells and mouse P815 mast cells respectively cultured in a medium supplemented with the third peptide group at different concentrations.
Figure 4B:
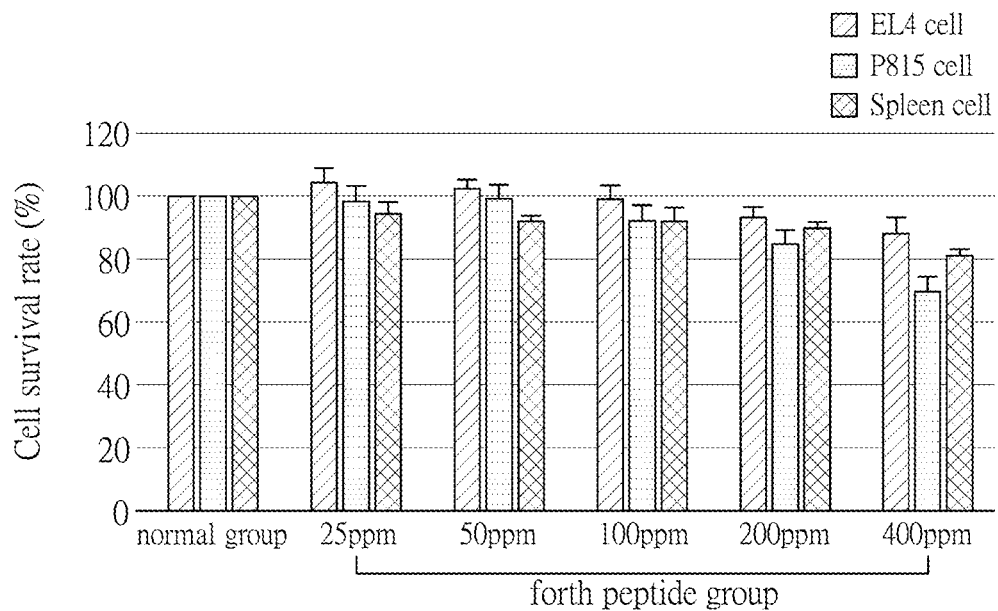
FIG. 4B is the result of detecting survival rates of mouse EL4 lymphoma cells and mouse P815 mast cells respectively cultured in a medium supplemented with the fourth peptide group at different concentrations.
Figure 4C:
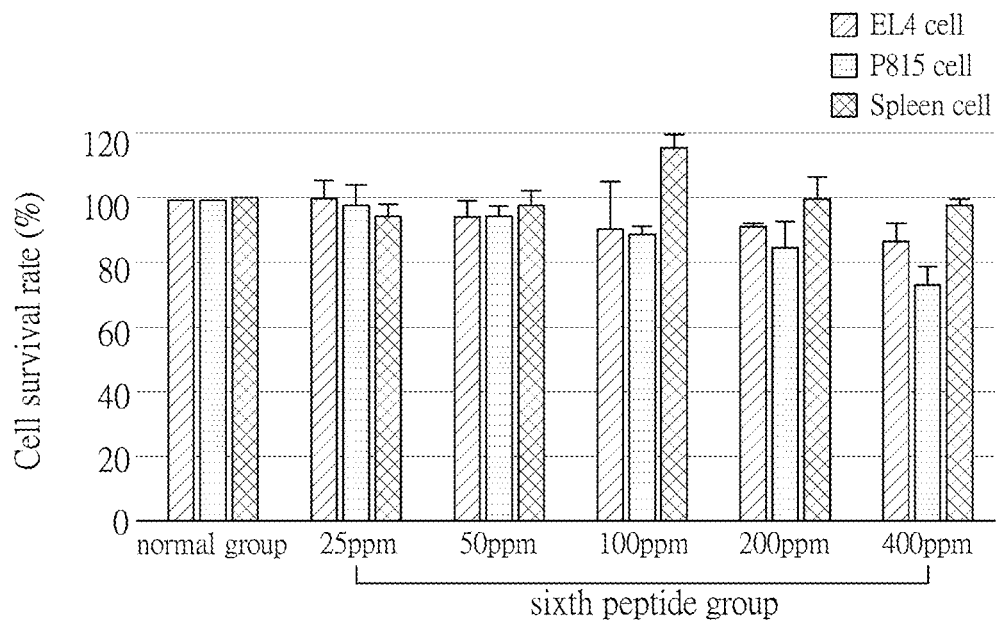
FIG. 4C is the result of detecting survival rates of mouse EL4 lymphoma cells and mouse P815 mast cells respectively cultured in a medium supplemented with the sixth peptide group at different concentrations.
Figure 4D:
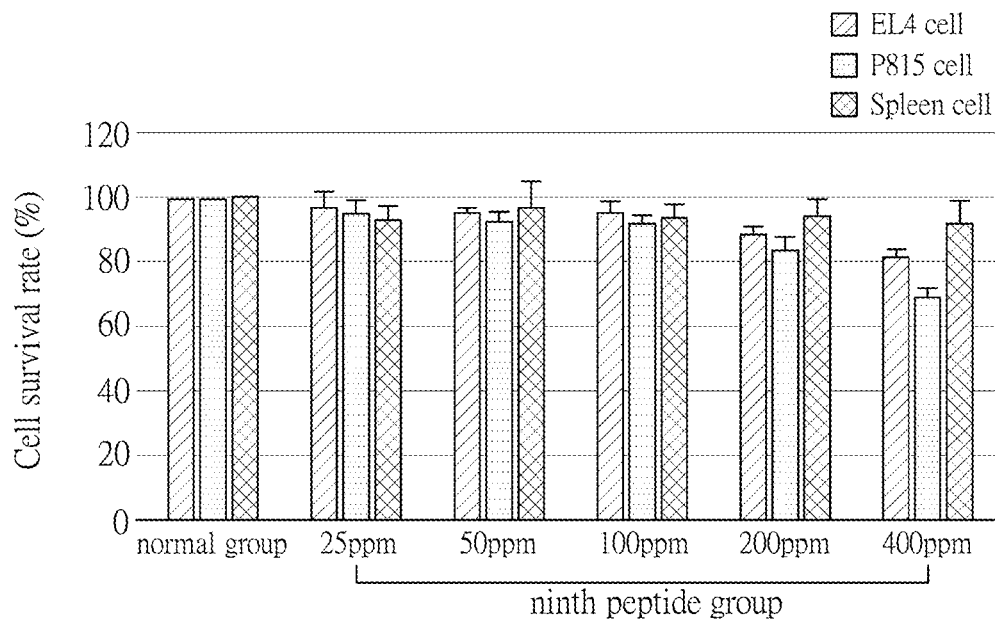
FIG. 4D is the result of detecting survival rates of mouse EL4 lymphoma cells and mouse P815 mast cells respectively cultured in a medium supplemented with the ninth peptide group at different concentrations.
Figure 4E:
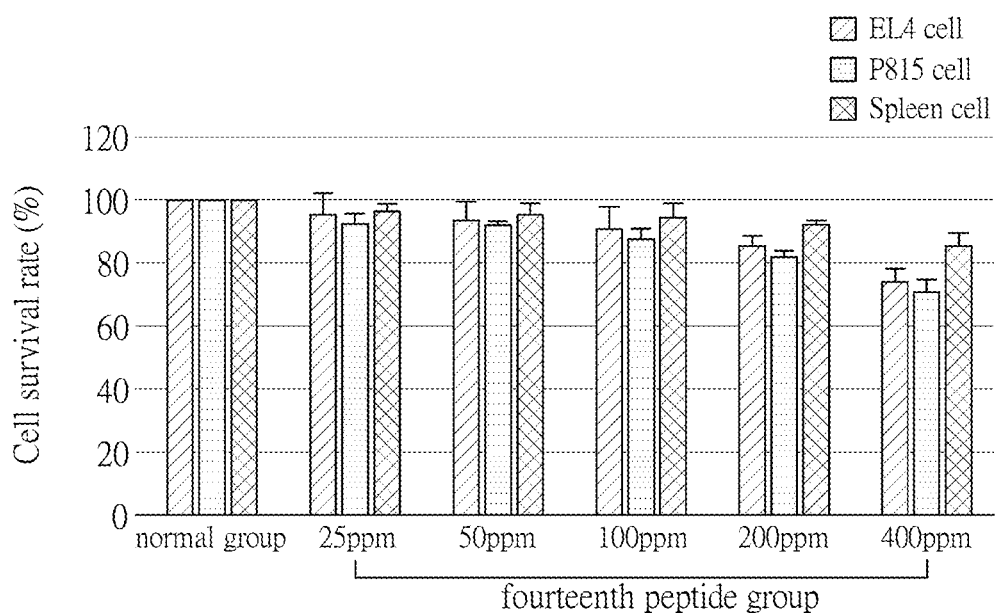
FIG. 4E is the result of detecting survival rates of mouse EL4 lymphoma cells and mouse P815 mast cells respectively cultured in a medium supplemented with the fourteenth peptide group at different concentrations.
Figure 5C:
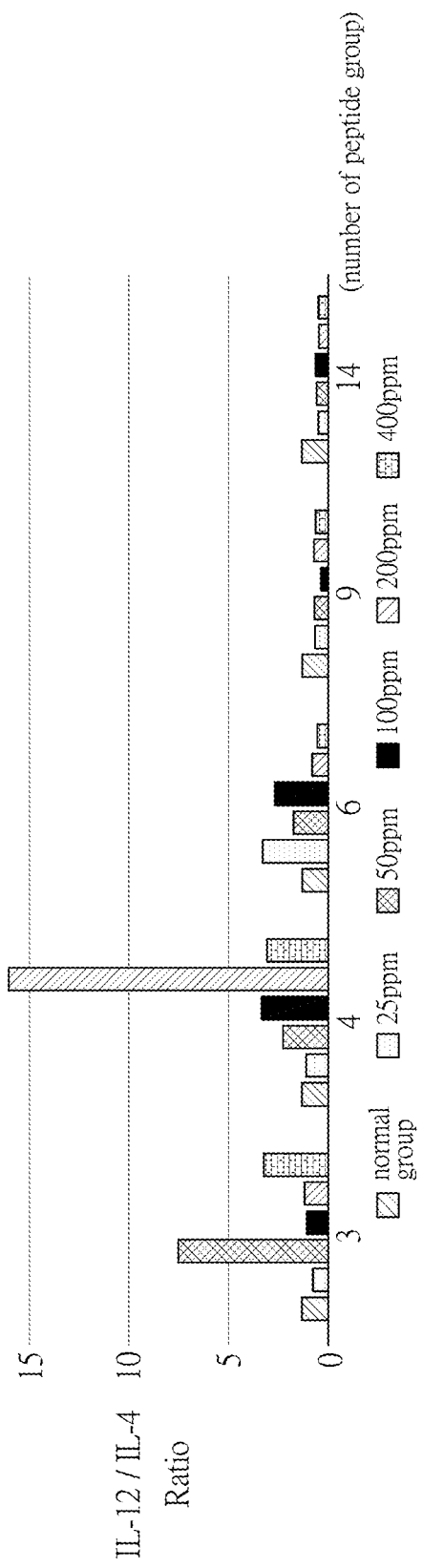
FIG. 5C is the analyzed result of a concentration ratio of IL-12/IL-4 secreted by the spleen cells of the mice in the OVA-induced group after the spleen cells of the mice in the OVA-induced group are respectively cultured in a medium supplemented with different concentrations of each of the peptide groups.
Figure 5D:
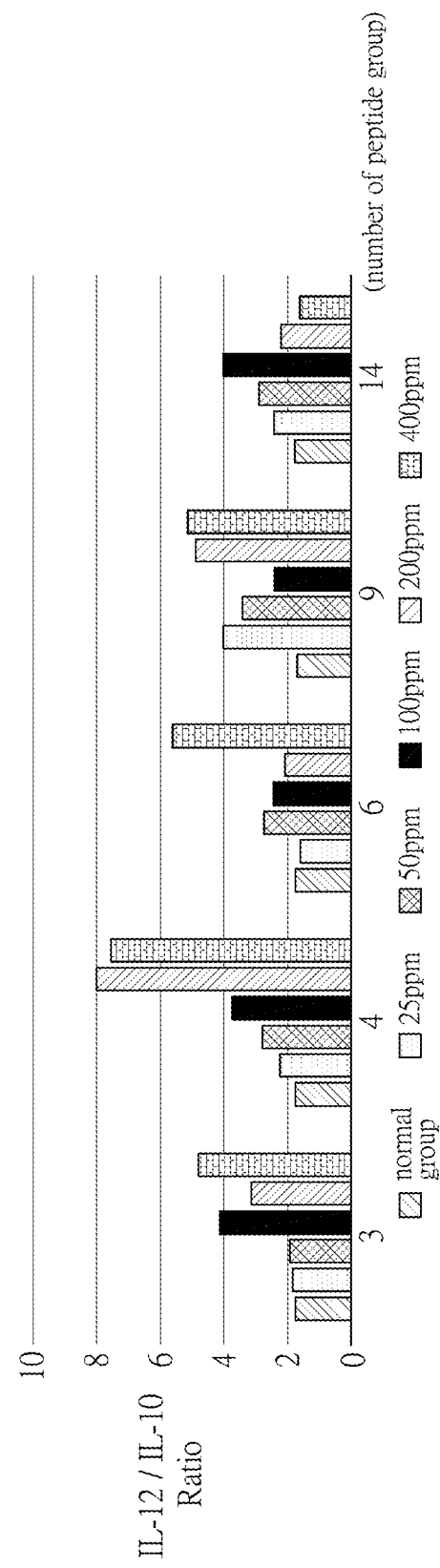
FIG. 5D is the analyzed result of a concentration ratio of IL-12/IL-10 secreted by the spleen cells of the mice in the OVA-induced group after the spleen cells of the mice in the OVA-induced group are respectively cultured in a medium supplemented with different concentrations of each of the peptide groups.

From the detection and analysis results shown in FIG. 3, the third peptide group, the fourth peptide group, the sixth peptide group, the ninth peptide group and the fourteenth peptide group are screened out to have an ability in inhibiting secretion of IL-4 and IL-13 cytokines, respectively.

Example 4: Safety Test

The five peptide groups screened out in Example 3 are added to a culture medium at concentrations of 0, 25, 50, 100, 200, and 400 ppm, respectively, and are used to culture mouse EL4 lymphoma cells and mouse P815 mast cells respectively, and then survival rates of the mouse EL4 lymphoma cells and the mouse P815 mast cells in different culture environments are detected respectively, the results are shown in FIG. 4A to FIG. 4E.

From the results of FIG. 4A to FIG. 4E, it can be known that the survival rates of the mouse EL4 lymphoma cells and/or the mouse P815 mast cells decrease when each of the peptide groups is added at a concentration of 400 ppm, while each of the peptide groups at a concentration of 200 ppm will not affect the survival rates of the mouse EL4 lymphoma cells and/or the mouse P815 mast cells; it shows that a highest safe dose of each of the peptide groups that can be used is 200 ppm.

Example 5: Animal Test (1)

Ten 6-week-old BALC/c mice are randomly divided into two groups, the normal group and the OVA (ovalbumin) induced group, wherein a preparation method of the mice in the OVA (ovalbumin) induced allergic group is as follows: 20 μl (20 μg) of ovalbumin (OVA 1 mg/mL 0.9% saline) solution and 25 μl (1 mg) aluminum hydroxide adjuvant aqueous solvent (Alum, 40 mg/mL) are mixed well. After supplementing the volume with 0.9% physiological saline to a dose of 0.1 mL/10 g mice, the mice are induced by intraperitoneal injection to make each of the mice generate specific antibodies, and then 5% ovalbumin is administered by aerosol to induce allergic reactions such as respiratory tract constriction in the mice.

After 7 days of sensitization induction, the mice in each of the groups are sacrificed. After sacrifice, IgE and IgG1 (Th2-related indicators) in the serum of the normal mice (normal group) and the OVA-induced allergic mice (OVA-induced group) are measured, it can be known that concentrations of IgE and IgG1 in the serum of the mice in the induced group are both higher than those of the normal mice, and the mice in the OVA-induced group have obvious symptoms of asthma, wherein the concentration of IgE in the serum of the mice in the OVA-induced group is more than ten times that of the normal mice, and the concentration of IgG1 in the serum of the mice in the OVA-induced group is more than double that of the normal mice; it can be known that OVA induction is capable of reliably establishing a sensitized animal model.

Each of the peptide groups is screened in Example 3 and added to a culture medium at concentrations of 0, 25, 50, 100, 200, and 400 ppm, respectively, and the spleen cells of the mice in the OVA induced group are placed in each culture medium for co-culture. After the culture is completed, concentrations of two Th1 hormones, IFN-γ and IL-12, and two Th2 hormones, IL-4 and IL-10, secreted by the cells in the culture medium of each of the groups are detected, and then concentration ratios of Th1/Th2 are calculated, that are IFN-γ/IL-4, IFN-γ/IL-10, IL-12/IL-4 and IL-12/IL-10, the results are shown in FIGS. 5A to 5D.

Combining the results of FIG. 5A to FIG. 5D, it can be known that the Th1/Th2 ratio adjusted by the third peptide group is 5-18 times that of the control group, the Th1/Th2 ratio adjusted by the fourth peptide group is 8-20 times that of the control group, the Th1/Th2 ratio adjusted by the sixth peptide group is 2.5-17 times that of the control group, and the Th1/Th2 ratio adjusted by the fourteenth peptide group is 7 times that of the control group. The results show that, except for the 9th peptide group, which has no obvious desensitization efficacy, the other four peptide groups have obvious desensitization efficacy, wherein the 3rd peptide group has the best desensitization efficacy.

Example 6: Sequence Identification

The peptide groups (the 3rd, 4th, 6th, and 14th peptide groups) with anti-allergy and immune regulation abilities screened in Example 5 are identified by a liquid chromatography tandem mass spectrometer (LC/MS/MS) for amino acid sequence composition, and then are separated according to mass differences of fragments, and the resulting mass spectral signals are compared in the database (Database ref. Matrix science) to obtain the peptides shown in Table 2 below.

TABLE 2

Peptide sequences from the peptide groups

| Peptide serial number | Amino acid sequence code | Amino acid sequence | Molecular weight (Da) |
|---|---|---|---|
| 1 | SEQ ID No: 1 | DLQLAGLIGL | 1012.2006 |
| 2 | SEQ ID No: 2 | NPALQVIKV | 981.1899 |
| 3 | SEQ ID No: 3 | GLGDAKVALGI | 1013.1887 |
| 4 | SEQ ID No: 4 | EWLLGLLGI | 1013.2341 |
| 5 | SEQ ID No: 5 | DLDVVVALGI | 1013.1854 |
| 6 | SEQ ID No: 6 | VGNSLAAVIIG | 1013.1887 |
| 7 | SEQ ID No: 7 | PMALLAVLGL | 997.2953 |
| 8 | SEQ ID No: 8 | NKKQAAALGI | 1013.1922 |
| 9 | SEQ ID No: 9 | GVSGGVLAAILG | 1013.1887 |
| 10 | SEQ ID No: 10 | TANAIGLAGLI | 1013.1887 |
| 11 | SEQ ID No: 11 | PPYQGAPLM | 973.1462 |
| 12 | SEQ ID No: 12 | KIVNQVNHLNPT | 1376.5604 |
| 13 | SEQ ID No: 13 | QTAQALVLIG | 1013.1887 |
| 14 | SEQ ID No: 14 | LVPWSIIGL | 997.2306 |
| 15 | SEQ ID No: 15 | ADALQLVLAV | 1012.2006 |
| 16 | SEQ ID No: 16 | TRQKALAALGI | 1141.3643 |

Example 7: Sequence Synthesis and Detection of Ability in Inhibiting Immune-Related Cytokines The peptides listed in Table 2 are synthesized into high purity (>90%) samples of their corresponding sequences by Fmoc method.

Referring to the method disclosed in Example 3, an ability of each of the above synthetic sequences in inhibiting secretion of cytokines such as IL-4 and IL-13 is tested, the results are shown in Table 3, where N represents that the results obtained have not decreased.

It can be known from the results in Table 3 that, the peptides disclosed in the invention with an amino acid sequence encoded as SEQ ID No: 1, SEQ ID No: 2, SEQ ID No: 3, SEQ ID No: 4, SEQ ID No: 5 are capable of inhibiting allergic reactions, wherein the peptides with an amino acid sequence encoded as SEQ ID No: 2, SEQ ID No: 3 and SEQ ID No: 5 have better effects in inhibiting secretion of IL-4 and IL-13 by cells.

TABLE 3

Detection of ability of each of the peptides in inhibiting secretion of cytokines

| Peptide serial number | Amino acid sequence code | IL-4 Concentration decrease percentage (%) | IL-13 Concentration decrease percentage (%) |
|---|---|---|---|
| 1 | SEQ ID No: 1 | 14.5 | 24.0 |
| 2 | SEQ ID No: 2 | 8.1 | 27.1 |
| 3 | SEQ ID No: 3 | 5.1 | 21.7 |
| 4 | SEQ ID No: 4 | 19.9 | 35.4 |
| 5 | SEQ ID No: 5 | 7.3 | 24.0 |
| 6 | SEQ ID No: 6 | 0.9 | 2.7 |
| 7 | SEQ ID No: 7 | 4.1 | 5.2 |
| 8 | SEQ ID No: 8 | 1.0 | 11.4 |
| 9 | SEQ ID No: 9 | 5.8 | 2.7 |
| 10 | SEQ ID No: 10 | 9.3 | N |
| 11 | SEQ ID No: 11 | 10.0 | N |
| 12 | SEQ ID No: 12 | N | 10.8 |
| 13 | SEQ ID No: 13 | N | 12.1 |
| 14 | SEQ ID No: 14 | N | 9.8 |
| 15 | SEQ ID No: 15 | 2.7 | 3.8 |
| 16 | SEQ ID No: 16 | N | 5.9 |

Example 8: Animal Test (2)

6-week-old BALC/c mice are randomly divided into five groups, the first group of mice are normal mice, and the second to fifth groups are mice with OVA-induced respiratory hyperresponsiveness (asthma mode). Except for the first group of mice, the other groups of mice are treated with the following conditions every day for two weeks before the test, and then are subjected to two immunization inductions with a one-week interval between the two immunization inductions. The mice in each of the groups are sacrificed 7 days after the test is completed, and the OVA-induced method is as described in Example 5, which will not be repeated here. Wherein the ratio of peptides with the amino acid sequences are coded as SEQ ID No.1, SEQ ID No.2, SEQ ID No.3, SEQ ID No.4, and SEQ ID No.5 is 0.1-1: 0.1-1:0.1-1:0.1-1:0.1-1, and the ratio of the peptide is nearly equal will be better, such as 1:1:1:1:1 or 1:0.9:0.9:0.9:1.

The second group is fed with phosphate buffer at a dose of 200 μl/mouse/day;

the third group is fed with peptide powder at a dose of 0.017 g/mouse/day, containing 15.198 ppm of the peptides;

the fourth group is fed with peptide powder at a dose of 0.034 g/mouse/day, containing 30.396 pm of the peptides; and the fifth group is fed with peptide powder at a dose of 0.068 g/mouse/day, containing 60.792 ppm of the peptides;

wherein the peptide group refers to the composition of the peptides disclosed in the invention with an amino acid sequence encoded as SEQ ID No: 1, SEQ ID No: 2, SEQ ID No: 3, SEQ ID No: 4, SEQ ID No: 5.

After the test, levels of IgE, IgG1, IgG2a and IgG2b in the serum of the mice in each of the groups are detected respectively, the results are shown in Table 4. It can be known from the results in Table 4 that, compared with the first group of the mice, the level of Th2-related antibodies IgE and IgG1 in the second group of the mice are significantly increased, indicating that the asthma animal model is successfully established; compared with the second group of the mice, the levels of IgE and IgG1 in the serum of the mice in the 3rd to 5th groups are significantly decreased, and the levels of IgG2a and IgG2b increase with an increase in a dose of the peptide group administered.

TABLE 4

Levels of IgE, IgG1, IgG2a and IgG2b in the serum of the mice in each of the groups

| Group | IgE (μg/ml) | IgG1 (μg/ml) | IgG2a (μg/ml) | IgG2b (μg/ml) |
|---|---|---|---|---|
| Group 1 | 0.84 ± 0.22 | 211.95 ± 5.02 | 68.83 ± 4.47 | 1518.24 ± 5.73 |
| Group 2 | 10.34 ± 4.36 | 13157.32 ± 12.80 | 124.22 ± 11.61 | 2207.62 ± 27.06 |
| Group 3 | 9.15 ± 3.56 | 6935.96 ± 26.77 | 145.9 ± 14.62 | 2235.81 ± 35.95 |
| Group 4 | 6.02 ± 1.69 | 4901.07 ± 58.19 | 158.27 ± 4.83 | 3180.24 ± 10.23 |
| Group 5 | 15.12 ± 2.37 | 5026 ± 39.71 | 462.76 ± 27.46 | 3463.86 ± 16.86 |

Example 9: Pulmonary Respiratory Resistance Test

In Example 8, the pulmonary respiratory resistance test is performed after the immunity of the mice in each of the groups is boosted for the last time, that is, the mice in each of the groups are respectively inhaled with different doses of methacholine by aerosol: 0, 6.25, 12.5, 25, 50 mg/mL, inhalation time is 3 minutes, and then gas changes inside and outside a specific space of the mice in each of the groups under the condition of clear consciousness are detected by adopting a non-invasive method to calculate inhalation and exhalation of gas volumes of the mice in order to further know a value of each respiratory parameter, such as maximum inspiratory volume, maximum expiratory volume, and expiratory time, to calculate the pulmonary function index Penh, the results are shown in Table 5 below.

It can be known from the results in Table 5 that, when methacholine is administered, the Penh values of the mice in the second group are increased compared with the Penh values of the mice in the first group, indicating that methacholine can indeed cause insufficiency of lung function in the mice. It can be known from the Penh values of the mice in the groups 3 to 5 that, by administering the peptide group disclosed in the invention is capable of effectively improving pulmonary function decline caused by methacholine. In other words, each of the peptides or the composition disclosed in the invention is capable of effectively improving pulmonary function impairment caused by allergy or asthma.

TABLE 5

Penh values after induction of hyperpnea in the mice in each of the groups

| Group | Methacholine (mg/mL) | | | | |
|---|---|---|---|---|---|
| | 0 | 6.25 | 12.5 | 25 | 50 |
| Group 1 | 0.391 | 0.366 | 0.598 | 0.523 | 0.502 |
| Group 2 | 0.339 | 0.688 | 1.421 | 3.158 | 4.280 |
| Group 3 | 0.307 | 0.535 | 0.566 | 0.605 | 0.839 |
| Group 4 | 0.339 | 0.687 | 0.644 | 0.870 | 1.069 |
| Group 5 | 0.307 | 0.614 | 0.755 | 0.860 | 0.908 |

Example 10: Spleen Cell Proliferative Response

The spleen cells of the mice in each of the groups in Example 8 are taken after the mice are sacrificed. The spleen cells of the mice in each of the groups are placed in a 96-well cell culture dish at $2\times10^5$ cells/well, and Concanavalin A (Con A), Lipopolysaccharide (LPS) and OVA are used to stimulate T, B and specific antigen-activated cell proliferation, after culturing at 37° C., 5% $CO_2$ for 48 hours, analyzed with Alamar blue, absorbances of the cells at 570 nm and 600 nm are measured, and a stimulation index is calculated, wherein the stimulation index is a ratio of a cell proliferation value to a value without adding; the stimulation index of the spleen cells of the mice in each of the groups is shown in Table 6 below.

It can be known from the results in Table 6 that, regardless of whether Concanavalin A, Lipopolysaccharide or OVA is used as an allergen, an immune cell proliferation ability of the mice in the groups 3 to 5 is significantly higher than that of the mice in the group 2, wherein when the T cells are stimulated with ConA to proliferate, the mice in the group 4 have the highest increase; and when OVA is used to stimulate specific antigen proliferation, increases in the groups 4 and 5 are higher.

TABLE 6

Stimulation index of spleen cells of the mice in each of the groups

| Group | Stimulation index | | | |
|---|---|---|---|---|
| | None | ConA 10 μg/ml | LPS 10 μg/ml | OVA 10 μg/ml |
| Group 1 | 100 ± 0.00 | 99.53 ± 1.40 | 101.82 ± 2.41 | 100.38 ± 7.33 |
| Group 2 | 102.24 ± 2.36 | 101.34 ± 3.73 | 111.27 ± 3.81 | 101.82 ± 4.77 |
| Group 3 | 190.33 ± 9.43 | 153.69 ± 7.29 | 0.566 | 196.89 ± 14.15 |
| Group 4 | 241.96 ± 3.90 | 251.11 ± 16.27 | 239.08 ± 12.59 | 236.28 ± 8.77 |
| Group 5 | 168.95 ± 2.88 | 167.02 ± 7.18 | 224.88 ± 15.02 | 240.38 ± 11.66 |

Furthermore, spleen cells (effector cells) and YAC-1 cells (target cells, $2\times10^4$ cells/well) of the mice in each of the groups are co-cultured at different ratios, wherein ratios of the spleen cells to the target cells are 5:1, 25:1, 50:1, culture conditions are 37° C., 5% $CO_2$, after 4 hours of culture, centrifuged at 250 g for 3 minutes, 50 μl of a supernatant liquid is taken, analyzed with LDH, and absorbance values are measured at 490 nm and 680 nm. Activities of natural killer cells in the spleen cells of the mice in each of the groups are shown in Table 7.

It can be known from the results in Table 7 that, when the ratios of the spleen cells to the target cells are 25:1 and 50:1, the activities of the natural killer cells in the spleen of the mice in the group 5 are significantly higher than those in the mice in the group 2.

TABLE 7

Activities of natural killer cells in spleen cells of the mice in each of the groups

| Group | Ratio of spleen cells to target cells | | |
|---|---|---|---|
| | 5 | 25 | 50 |
| Group 1 | 6.70 ± 1.95 | 18.9 ± 5.48 | 37.92 ± 9.03 |
| Group 2 | 5.63 ± 2.66 | 19.53 ± 2.12 | 38.67 ± 2.75 |
| Group 3 | 2.6 ± 1.59 | 15.98 ± 1.38 | 40.89 ± 4.37 |
| Group 4 | 4.69 ± 0.53 | 18.45 ± 1.39 | 42.43 ± 3.59 |
| Group 5 | 6.52 ± 2.29 | 32.07 ± 2.73 | 45.60 ± 3.70 |

Example 11: Analysis of Respiratory Lung Flushing Fluid

Lung flushing fluid of the mice in each of the groups in Example 8 is taken, and the levels of cytokines such as IL4, IL5, INFγ and IL12 are detected. The results are shown in Table 8.

The results in Table 8 show that compared with the mice in the first group, the Th2 cell-related cytokines: IL4 and IL5 in the lung flushing fluid of the mice in the second group are significantly increased, and the Th1 cell-related cytokines: IFN-γ and IL-12 are significantly decreased; and compared with mice in the group 2, the Th2 cell-related cytokines: IL4 and IL5 in the lung flushing fluid of the mice in the groups 3 to 5 are significantly decreased, respectively, and the Th1 cell-related cytokines: IFN-γ and IL-12 in the lung flushing fluid of the mice in the groups 4 to 5 are significantly increased, respectively.

TABLE 8

Cytokine level in lung flushing fluid of the mice in each of the groups

| Group | IL4 | IL5 | IFN-γ | IL-12 |
| --- | --- | --- | --- | --- |
| Group 1 | 39.47 ± 3.77 | 29.88 ± 9.68 | 68.90 ± 4.90 | 90.11 ± 9.64 |
| Group 2 | 189.69 ± 8.57 | 83.63 ± 14.36 | 42.95 ± 9.85 | 61.71 ± 9.97 |
| Group 3 | 138.80 ± 6.30 | 87.38 ± 13.17 | 66.78 ± 8.56 | 64.57 ± 9.33 |
| Group 4 | 66.13 ± 9.98 | 41.14 ± 12.47 | 81.24 ± 4.86 | 98.14 ± 12.31 |
| Group 5 | 43.91 ± 13.42 | 28.31 ± 5.93 | 167.89 ± 12.01 | 139.21 ± 2.47 |

Example 12: Analysis of Cytokine Secretion Function

Single-suspended spleen cells from the mice in each of the groups in Example 8 are cultured at 1×10⁶ cells/well, wherein culture conditions are 37° C., 5% $CO_2$, and culture time is 72 hours. After cultivation, centrifuged at 1200 rpm and 15° C. for 10 minutes, a supernatant liquid is taken for ELISA analysis to calculate the levels of cytokines such as IL4, IL5, INFγ and IL12 in the spleen cells of the mice in each of the groups after in vitro culture. The results are shown in Table 9.

From the results in Table 9, it can be known that compared with the mice in the first group, the Th2 cell-related cytokines IL4 and IL5 in the spleen cells of the mice in the second group induced by OVA are significantly increased, and the Th1 cell-related cytokines IFN-γ and IL-12 are significantly decreased; the Th2 cell-related cytokines IL4 and IL5 in the spleen cells of the mice in the group 3 and group 4, which are administered with the peptide groups, are significantly lower than those in the mice in the group 2 respectively; compared with the mice in the group 2, the levels of the Th1 cell-related cytokines IFN-γ and IL-12 in the spleen cells of the mice in the group 4 and group 5 are increased with increasing doses of the peptide groups administered. Further, in the spleen cells of the mice in the groups 3 to 5, the ratios of IFN-γ/IL4 increase with increasing doses of the peptide groups administered.

It can be known from the above results that the peptides disclosed in the invention or the peptide groups composed of the peptides have an efficacy of immune regulation, and have excellent immunity efficacy.

TABLE 9

Cytokine level of spleen cells of the mice in each of the groups after in vitro culture

| Group | IL4 | IL5 | IFN-γ | IL-12 |
| --- | --- | --- | --- | --- |
| Group 1 | 49.33 ± 14.67 | 114.25 ± 2.65 | 116.70 ± 5.25 | 98.73 ± 7.07 |
| Group 2 | 170.77 ± 6.73 | 423.00 ± 6.63 | 59.75 ± 7.70 | 22.36 ± 3.38 |
| Group 3 | 109.87 ± 10.62 | 313.42 ± 12.83 | 45.09 ± 2.36 | 42.36 ± 4.38 |
| Group 4 | 57.62 ± 1.53 | 126.75 ± 9.62 | 104.31 ± 7.48 | 150.24 ± 9.65 |
| Group 5 | 98.34 ± 7.40 | 383.00 ± 19 | 221.09 ± 9.62 | 189.64 ± 3.86 |

What is claimed is:

1. A method for immune regulation or anti-allergy, comprising administering a composition including an effective amount of isolated peptides with amino acid sequences being encoded as SEQ ID No: 1, SEQ ID No: 2, SEQ ID No: 3, SEQ ID No: 4 and SEQ ID No: 5 to an individual with allergic disease.

2. The method for immune regulation or anti-allergy as claimed in claim 1, wherein the allergic disease is allergy or asthma.

* * * * *

```
SEQUENCE LISTING

Sequence total quantity: 16
SEQ ID NO: 1           moltype = AA  length = 10
FEATURE                Location/Qualifiers
source                 1..10
                       mol_type = protein
                       organism = synthetic construct
SEQUENCE: 1
DLQLAGLIGL                                                             10

SEQ ID NO: 2           moltype = AA  length = 9
FEATURE                Location/Qualifiers
source                 1..9
                       mol_type = protein
                       organism = synthetic construct
SEQUENCE: 2
NPALQVIKV                                                              9

SEQ ID NO: 3           moltype = AA  length = 11
FEATURE                Location/Qualifiers
source                 1..11
                       mol_type = protein
                       organism = synthetic construct
SEQUENCE: 3
GLGDAKVALG I                                                           11
```

-continued

| | | |
|---|---|---|
| SEQ ID NO: 4<br>FEATURE<br>source | moltype = AA length = 9<br>Location/Qualifiers<br>1..9<br>mol_type = protein<br>organism = synthetic construct | |
| SEQUENCE: 4<br>EWLLGLLGI | | 9 |
| SEQ ID NO: 5<br>FEATURE<br>source | moltype = AA length = 10<br>Location/Qualifiers<br>1..10<br>mol_type = protein<br>organism = synthetic construct | |
| SEQUENCE: 5<br>DLDVVVALGI | | 10 |
| SEQ ID NO: 6<br>FEATURE<br>source | moltype = AA length = 11<br>Location/Qualifiers<br>1..11<br>mol_type = protein<br>organism = synthetic construct | |
| SEQUENCE: 6<br>VGNSLAAVII G | | 11 |
| SEQ ID NO: 7<br>FEATURE<br>source | moltype = AA length = 10<br>Location/Qualifiers<br>1..10<br>mol_type = protein<br>organism = synthetic construct | |
| SEQUENCE: 7<br>PMALLAVLGL | | 10 |
| SEQ ID NO: 8<br>FEATURE<br>source | moltype = AA length = 10<br>Location/Qualifiers<br>1..10<br>mol_type = protein<br>organism = synthetic construct | |
| SEQUENCE: 8<br>NKKQAAALGI | | 10 |
| SEQ ID NO: 9<br>FEATURE<br>source | moltype = AA length = 12<br>Location/Qualifiers<br>1..12<br>mol_type = protein<br>organism = synthetic construct | |
| SEQUENCE: 9<br>GVSGGVLAAI LG | | 12 |
| SEQ ID NO: 10<br>FEATURE<br>source | moltype = AA length = 11<br>Location/Qualifiers<br>1..11<br>mol_type = protein<br>organism = synthetic construct | |
| SEQUENCE: 10<br>TANAIGLAGL I | | 11 |
| SEQ ID NO: 11<br>FEATURE<br>source | moltype = AA length = 9<br>Location/Qualifiers<br>1..9<br>mol_type = protein<br>organism = synthetic construct | |
| SEQUENCE: 11<br>PPYQGAPLM | | 9 |
| SEQ ID NO: 12<br>FEATURE<br>source | moltype = AA length = 12<br>Location/Qualifiers<br>1..12<br>mol_type = protein<br>organism = synthetic construct | |
| SEQUENCE: 12<br>KIVNQVNHLN PT | | 12 |
| SEQ ID NO: 13<br>FEATURE<br>source | moltype = AA length = 10<br>Location/Qualifiers<br>1..10<br>mol_type = protein<br>organism = synthetic construct | |
| SEQUENCE: 13<br>QTAQALVLIG | | 10 |

```
SEQ ID NO: 14              moltype = AA  length = 9
FEATURE                    Location/Qualifiers
source                     1..9
                           mol_type = protein
                           organism = synthetic construct
SEQUENCE: 14
LVPWSIIGL                                                                  9

SEQ ID NO: 15              moltype = AA  length = 10
FEATURE                    Location/Qualifiers
source                     1..10
                           mol_type = protein
                           organism = synthetic construct
SEQUENCE: 15
ADALQLVLAV                                                                10

SEQ ID NO: 16              moltype = AA  length = 11
FEATURE                    Location/Qualifiers
source                     1..11
                           mol_type = protein
                           organism = synthetic construct
SEQUENCE: 16
TRQKALAALG I                                                              11
```